US006534079B1

(12) United States Patent
Munagavalasa

(10) Patent No.: US 6,534,079 B1
(45) Date of Patent: Mar. 18, 2003

(54) PASSIVE SPACE INSECT REPELLANT STRIP

(75) Inventor: Murthy S. Munagavalasa, Racine, WI (US)

(73) Assignee: S. C. Johnson & Son, Inc., Racine, WI (US)

( * ) Notice: Subject to any disclaimer, the term of this patent is extended or adjusted under 35 U.S.C. 154(b) by 0 days.

(21) Appl. No.: 09/326,446

(22) Filed: Jun. 4, 1999

(51) Int. Cl.[7] .......... A01N 25/10

(52) U.S. Cl. .......... 424/409; 424/411; 514/531

(58) Field of Search .......... 514/531; 424/405, 424/409, 411, 417–421

(56) References Cited

U.S. PATENT DOCUMENTS

| | | | | |
|---|---|---|---|---|
| 339,810 A | | 4/1886 | Regan | |
| 2,720,013 A | | 10/1955 | Clarke | 21/126 |
| 2,956,073 A | | 10/1960 | Whetstone et al. | 160/461 |
| 3,044,885 A | | 7/1962 | Loehr et al. | 99/154 |
| 3,116,201 A | | 12/1963 | Whetstone et al. | 167/22 |
| 3,295,246 A | | 1/1967 | Landsman et al. | 43/131 |
| 3,318,769 A | | 5/1967 | Folckemer et al. | 167/42 |
| 3,620,453 A | * | 11/1971 | Gancberg et al. | 424/421 |
| 4,103,450 A | | 8/1978 | Whitcomb | 43/131 |
| 4,178,384 A | | 12/1979 | Ensing | 424/305 |
| 4,439,415 A | | 3/1984 | Hennart et al. | 424/16 |
| 4,631,231 A | | 12/1986 | Stendel et al. | 428/413 |
| 4,765,982 A | | 8/1988 | Ronning et al. | 424/403 |
| 4,796,381 A | | 1/1989 | Kauth et al. | 43/124 |
| 4,860,488 A | | 8/1989 | Shigetoyo | 43/129 |
| 4,879,117 A | | 11/1989 | Rombi | 424/411 |
| 4,889,872 A | * | 12/1989 | Naumann et al. | 514/531 |
| 4,900,876 A | | 2/1990 | Bushman et al. | 119/106 |
| 4,901,674 A | | 2/1990 | Bushman et al. | 119/106 |
| 4,940,729 A | | 7/1990 | Matthewson | 514/531 |
| 4,966,796 A | | 10/1990 | Aki et al. | 428/34.3 |
| 5,091,183 A | | 2/1992 | Yano et al. | 424/405 |
| 5,156,843 A | | 10/1992 | Leong et al. | 424/411 |
| 5,198,287 A | | 3/1993 | Samson et al. | 428/248 |
| 5,229,122 A | | 7/1993 | Chadwick et al. | 424/408 |
| 5,252,387 A | | 10/1993 | Samson et al. | 428/245 |
| 5,290,770 A | | 3/1994 | Matthewson | 514/86 |

FOREIGN PATENT DOCUMENTS

| | | |
|---|---|---|
| DE | 19530076 | 2/1997 |
| DE | 19947146 | 5/2000 |
| EP | 0253640 A3 | 1/1988 |

(List continued on next page.)

OTHER PUBLICATIONS

XP002149732, Derwent Publications Ltd., London, Great Britain, May 28, 1992.

Database WPI, Section CH, Week 9013, Derwent Publications Ltd., London, GB; An 90–096004; Derwent Abstract for JP,A,02 048 507 (Sumitomo Chem. Ind. KK).

Pflanzenschutz Nachrichten Bayer (Special Edition), Published by Bayer AG, Copyright 1995 by Bayer AG, Laverkusen.

*Primary Examiner*—Neil S. Levy

(57) ABSTRACT

An insect control article to control flying insects. The insect control article has a non-absorptive and inert substrate that is coated with an active insect control ingredient that is available for passive evaporation. The active insect control ingredient is selected from the group consisting of transfluthrin, tefluthrin, and combinations thereof. The method of the invention for controlling flying insects includes providing an insect control article having a non-absorptive, inert substrate that is coated with an active insect control ingredient available for passive evaporation, wherein the active insect control ingredient is selected from the group consisting of transfluthrin, tefluthrin, and combinations thereof. The insect control article is then placed in an environment in such a manner that the substrate of the insect control article is exposed to non-augmented air movement, and the active insect control ingredient coated on the substrate is allowed to evaporate passively into the air.

10 Claims, 5 Drawing Sheets

FOREIGN PATENT DOCUMENTS

| | | | | |
|---|---|---|---|---|
| EP | 0596317 | A1 | | 5/1994 |
| EP | 0775441 | A1 | | 5/1997 |
| EP | 0925717 | | * | 1/1999 |
| EP | 0916262 | | | 5/1999 |
| GB | 1236343 | | | 6/1971 |
| GB | 2151926 | A | | 7/1985 |
| GB | 2276320 | A | | 9/1994 |
| WO | WO96/32843 | | | 10/1996 |
| ZA | 711214 | | | 2/1971 |

* cited by examiner

PASSIVE SPACE INSECT REPELLANT STRIP

BACKGROUND OF THE INVENTION

The present invention relates generally to insect control and more particularly to passive insect control articles that are effective in killing or repelling mosquitoes.

For certain applications, it is important to be able to control flying insects for six to ten hour or even longer periods within defined areas such as the enclosed space of a bedroom. Such a duration of insect control is desirable, for example, to protect a sleeper occupying an unscreened room from mosquitoes for a single night. It is also useful to be able to deliver an insect controlling amount of active ingredient nightly for multiple nights in succession. Successful flying insect control is also useful in other living spaces, including screened areas that for any reason are still subject to invasion by flying insects, as well as outdoor areas such as a patio, or the like.

Traditionally, articles or devices that dispense insecticide vapors to control insects in such settings require heating or burning a liquid or solid substrate to evaporate the active ingredients. For example, conventional citronella candles have long been used for such purposes. Burning insect coils are also commonly used to achieve a night's insect control or to control mosquitoes or other insects in outdoor areas. The product sold by S. C. Johnson & Son, Inc. of Racine, Wis. under the trademark "45 Nights" is an example of a type of product known in the art for delivering insect control over repeated periods of use, such as a nightly use in an unscreened bedroom. The "45 Nights" product is an example of conventional heated, liquid evaporation insect control products.

The products referred to above all can be effective, within certain limits. However, products that require a heat source also require a safe burning site, e.g. in the case of insect coils, or may require a source of house electrical current for typical heated evaporation products. Products exist that are designed to avoid some of these difficulties by employing passive evaporation of insect control active ingredients without the application of heat. However, they have problems and limitations when compared to insect control strategies employing products requiring the application of heat.

For example, Regan, U.S. Pat. No. 339,810 uses a tobacco preparation as a repellent that is first soaked into cloth or paper and then dried. The repellent active ingredient is reported to evaporate from the substrate to repel insects. More recent technology such as that disclosed in Landsman et al, U.S. Pat. No. 3,295,246 has included the use of pyrethrum or pyrethroid materials as passively evaporated insect control active ingredients. Ensing, U.S. Pat. No. 4,178,384 employs pyrethroids as repellents applied to the locus to be protected.

Whitcomb, U.S. Pat. No. 4,130,450 describes an insecticide-impregnated, open, low-density web that provides an expanded surface that may be loaded with contact insecticides, including pyrethrum and synthetically prepared insecticides. Whitcomb prefers the use of micro-encapsulated pyrethrum to avoid pyrethrum instability when exposed to ultraviolet light and oxygen. Whitcomb mentions that the web may be hung to permit vaporization of the active ingredient to combat flies. Similarly, Chadwick et al, U.S. Pat. No. 5,229,122 utilizes a mixture of micro-encapsulated and non-micro-encapsulated active ingredients, noting that any known pesticide may be used for the purpose. Pyrethrunim or a pyrethroid equivalent are referred to as possible pesticides. The preparation is used to coat surfaces, although it is also noted that the vapor phase of the pesticides may be valuable.

Kauth et al, U.S. Pat. No. 4,796,381, is an example of the use of paper or textile strips impregnated with insecticide that is allowed to evaporate to control insect pests. The Kauth et al materials utilize pyrethroids and, in particular, vaporthrin, permethrin, and bioallethrin. However, the devices of Kauth et al are designed to be hung in closets or placed in drawers, suggesting that they are understood to be inadequate to protect larger, more open spaces. Nothing in Kauth et al suggests any ability of their paper or textile strips to control insects in relatively large air spaces.

Samson et al, U.S. Pat. Nos. 5,198,287 and 5,252,387 disclose a fabric for use in a tent, the fabric including a coating that contains evaporable insecticides, and in particular, permethrin. Again, a confined space is being protected.

Aki et al, U.S. Pat. No. 4,966,796, utilizes a pyrethroid insecticide on kraft paper, with additional layers of untreated kraft paper added to create a material useful for making an insect-resistive packaging material or bag.

Landsman et al U.S. Pat. No. 3,295,246 teaches the use of an insecticide-soaked and then dried paper that is coated with resin to slow evaporation of the active ingredient. The resin coating is deemed important to make an insecticide product that will be effective over a long period of time. Example formulations cited in Landsman et al include pyrethrins as active ingredients. The Landsman et al product is not intended to protect large volumes of air and is also an example of the difficulty known in the art of achieving protection over an extended period of time because of the evaporative rate of active ingredients.

Ronning et al, U.S. Pat. No. 4,765,982 is an example of the use of micro encapsulated active ingredients to achieve a sustained release insect control effect. Pyrethroids, either synthetic or "natural," are cited as useful. The Ronning et al insecticidal device may be hung in the open to achieve a repellent effect in a restricted locale to drive insects from a nest or the like.

Yano et al, U.S. Pat. No. 5,091,183 and Matthewson, U.S. Pat. Nos. 4,940,729 and 5,290,774 cite specific insecticidal compounds for volatilization. Yano et al specifically discusses the use of impregnated papers for heatless evaporation of an insecticidal compound.

Clarke, U.S. Pat. No. 2,720,013, describes the use of a fabric material into which active ingredients are pressed or fused. Pyrethrum is cited as useful not by itself but as at least one element in a mixture of insecticides. The Clarke fabric material is designed to be adhered to the blades of an electric fan so that the insecticide will be directed into the area ventilated by the fan.

Emmrich et al WO96/32843 describes an insect control article to control flying insects comprising a substrate that is impregnated with an active insect control ingredient available for passive evaporation, wherein the active insect control ingredient is selected from transfluthrin, prallethrin, vapothrin, tefluthrin, esbiothrin, dichlovos (DDVP), and combinations thereof. Emmrich et al teaches that the insect control article must then be placed in an environment with significant air currents in such a manner that the substrate of the insect control article is exposed to the air currents, and the active insect control ingredient impregnated within the substrate is allowed to evaporate passively into the air. These air currents are referred to as "significant" since they are caused by either augmenting air movement via a fan, blower, etc. or the air movement is non-augmented but has a relatively strong natural air current such as that occurring when wind blows through an open window or door. Emmrich et al's insect control article does not require any external heat be applied to the article to vaporize the active ingredient although heat will, of course, aid in the rate of evaporation of the active from the substrate.

Another device not requiring heat but requiring a relatively strong augmented air current is taught by Ito in EP0775441. This device includes a carrier supporting a substrate containing a pesticide that is hard to vaporize at normal temperatures, and a blower for developing an air current across the substrate.

As seen from the above prior art, although passive evaporation of insecticides is known in the art, the nature of those materials has been such that the attention of the art generally has been directed to their application to closely restricted spaces or to the area in the immediate vicinity of the materials or to methods of use requiring fans, significant air currents or the like. Within that context, the art has focused on the need to provide for artificially extending the longevity of insect control by use of a slow release structure or regimen of some sort, or the like. Heat or augmented air movement and not passive evaporation have been the predominant means to achieve practical distribution of insecticide throughout a large volume of air, and heated evaporation from a liquid reservoir has been the practical means of achieving protection over a multiplicity of days.

As discussed above, currently available insect space repellent products typically require heat to drive the active into the ambient (e.g., coils, electric mats, liquid vaporizers, and citronella candles). These products demand either electric energy or chemical energy to vaporize the relatively low volatile actives. Products that run on electric energy cannot be used effectively in regions where there is scarcity of power supply. In addition, since such products are relatively expensive to consumers in such regions, less expensive insecticidal coils are typically used in these areas. However, excessive smoke, a burning tip, and residual ash are undesirable. A low-cost passive type of product, which requires no electricity or battery for heating, has no burning tip or residual ash, and does not release smoke would be most suitable for this segment of the market. However, as previously noted herein, a major problem with such passive insect control articles has been insufficient release rates due to low volatility of the actives and their substantial solubility in the substrate which limits the use of commercially available products based on passive evaporation technology to small enclosures such as closets or to arrangements which require augmented air movement to increase the release rate of the active.

SUMMARY OF THE INVENTION

Theoretically, any insecticide active when applied on any surface can be made to effectively control insects if sufficiently large quantity of the active is applied over a relatively large macro surface area. This technology becomes impractical and cost prohibitive under such circumstances because typically, a large amount of insecticide is absorbed or solubilized and entrapped into the substrate and only a portion of it is readily released into the air. Furthermore, the substrate needs to be very large which adds to the cost. This theoretical knowledge therefore cannot be put to practical commercial use. The present discovery specifically relates to making the passive evaporation technology work effectively at very low dose levels distributed over reasonable areas. For this, it is not only necessary to choose the right active, but also the right substrate and a right solvent. The right active is the one that is most effective against flying insects at low concentrations and has sufficient volatility to attain these concentrations. The right substrate is the one which provides the least resistance to the diffusion of active into the ambient. The right solvent is the one which solubilizes the active, distributes the active on the surface of the substrate uniformly, does not attack the substrate, and volatilizes itself rapidly without substantially volatilizing the active itself.

The insect control article of the present invention to control flying insects essentially comprises a non-absorbing and inert substrate coated with an active insect control ingredient that is available for passive evaporation. The active insect control ingredient is selected from the group consisting of transfluthrin, tefluthrin, and combinations thereof. Preferably, the active insect control ingredient includes at least one of transfluthrin and tefluthrin, and most preferably the active control ingredient includes at least transfluthrin.

When an active is absorbed or solubilized in the substrate, passive evaporation becomes substantially difficult due to additional mass transfer resistances encountered due to the substrate. However, if the solubility of the active is lower than 40 micrograms per square centimeter of the substrate, and preferably less than or equal to about 20 $\mu g/cm^2$, during practical applications, the active predominantly resides on the surface of the substrate and hence is readily available for evaporation. The substrate in this case does not provide any additional significant resistance to diffusion of the active into the environment. This particular substrate characteristic also enables the active to volatilize most uniformly until all the active evaporates from the surface of the substrate. Otherwise, typically, an absorbing substrate or a substrate with high solubility of active (or a substrate with both these characteristics) would release the active only partially, and in addition, in a non-uniform fashion.

The method of the invention for controlling flying insects includes the initial step of providing an insect control article having a non-absorbing and inert substrate that is coated with an active insect control ingredient available for passive evaporation, wherein the active insect control ingredient is selected from the group consisting of transfluthrin, tefluthrin, and combinations thereof. Preferably, the active insect control ingredient includes at least one of transfluthrin and tefluthrin, and most preferably the active control ingredient includes at least transfluthrin. Preferably the active is applied by means of a carrier solvent with low Hansen's hydrogen bonding parameter. The insect control article is then placed in an environment such as a bedroom in such a manner that the substrate of the insect control article is exposed to non-augmented air movements. The active insect control ingredient coated on the substrate then is allowed to evaporate passively into the air without the aid of a mechanical device such as heater or fan, preferably at a release rate of at least 0.2 mg/hr for any desirable duration.

Transfluthrin (also called Bayothrin or NAK 4455) has high potency against mosquitoes, flies, cockroaches, and moths. The chemical name of transfluthrin is (IR-trans)-(2,3,5,6-tetrafluorophenyl)methyl 3-(2,2-dichoroethenyl)-2,2-dimethyl cyclopropane carboxylate. Its extremely rapid knock-down property, even at very low concentrations and application rates, makes this chemical particularly suitable for passive evaporation technology. Unlike the prior art, passive evaporation technology in accordance with the present invention effectively controls flying insects even though it only utilizes non-augmented or insignificant natural air movements and diffusion as a means of releasing effective levels of active to provide the desirable repellency effect. The present invention provides the appropriate combination of substrate, solvent, and coating density that gives optimal efficacy at minimal cost. Specifically, the present invention teaches (a) that some materials are better than others for use as the substrate due to their physical and chemical resistance to the active, (b) that non-absorbing substrates release active more uniformly than absorbing substrates, (c) that carrier solvents with low Hansen hydrogen bonding and dispersive parameters and low volatility improve repellent strip efficacy, and (d) that biological efficacy remains substantially constant over time when the coating density lies in a certain range.

BRIEF DESCRIPTION OF THE SEVERAL VIEWS OF THE DRAWING

In the drawings:

FIG. 1(*b*) is a schematic illustration of a substrate for a second embodiment of a passive space insect repellant strip not coated with an active insect control ingredient and constructed with a surface having capillary grooves formed therein in accordance with the present invention;

FIG. 1(*c*) is a schematic illustration of a substrate for a third embodiment of a passive space insect repellant strip not coated with an active insect control ingredient and constructed with a surface having a mesh-like structure formed therein in accordance with the present invention;

FIG. 1(*d*) is a schematic illustration of a substrate for a fourth embodiment of a passive space insect repellant strip not coated with an active insect control ingredient and constructed with a textured surface in accordance with the present invention;

FIG. 1(*e*) is a schematic illustration of a substrate for a fifth embodiment of a passive space insect repellant strip not coated with an active insect control ingredient and constructed with a reticulated surface having capillary grooves on the inside surfaces of the openings formed in the substrate in accordance with the present invention;

FIG. 1(*f*) is an enlarged fragmentary view of a pair of openings in the substrate of FIG. 1(*e*) illustrating the capillary grooves formed on the inside surfaces of the openings;

FIG. 1(*g*) is a schematic illustration of a substrate for a sixth embodiment of a passive space insect repellant strip not coated with an active insect control ingredient and constructed with a reticulated surface having texture on the inside surfaces of the openings formed in the substrate in accordance with the present invention;

FIG. 1(*h*) is an enlarged fragmentary view of a pair of openings in the substrate of FIG. 1(*g*) illustrating the texture formed on the inside surfaces of the openings;

FIG. 1(*i*) is a schematic illustration of a substrate for a seventh embodiment of a passive space insect repellant strip not coated with an active insect control ingredient and constructed with a reticulated surface having texture on the outside surface of the substrate as well as texture on the inside surfaces of the openings formed in the substrate in accordance with the present invention;

FIG. 1(*j*) is an enlarged fragmentary view of a pair of openings in the substrate of FIG. 1(I) illustrating the texture formed on the inside surfaces of the openings as well as the texture on the outside surface of the substrate;

FIG. 1(*k*) is a schematic illustration of a substrate for an eighth embodiment of a passive space insect repellant strip not coated with an active insect control ingredient and constructed with a reticulated surface without any texture or capillary grooves on the inside surfaces of the openings formed in the substrate or on the outside surface of the substrate in accordance with the present invention;

FIG. 1(*l*) is a schematic illustration of a substrate for a ninth embodiment of a passive space insect repellant strip not coated with an active insect control ingredient and constructed with a reticulated surface having capillary grooves on the outside surface of the substrate as well as capillary grooves on the inside surfaces of the openings formed in the substrate in accordance with the present invention; and FIG. 1(*m*) is an enlarged fragmentary view of a pair of openings in the substrate of FIG. 1(*l*) illustrating the capillary grooves formed on the inside surfaces of the openings as well as the capillary grooves on the outside surface of the substrate;

DETAILED DESCRIPTION OF THE INVENTION

Figure 1A:
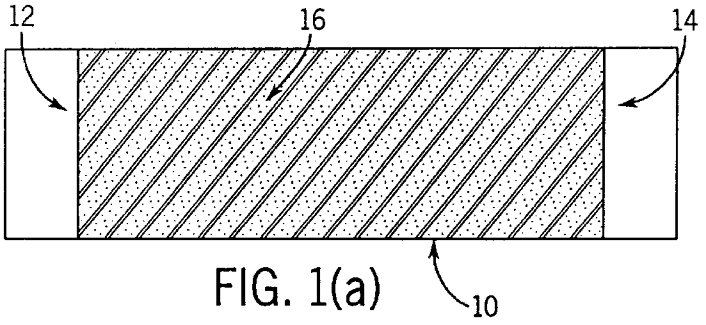
FIG. 1(*a*) is a schematic illustration of a passive space insect repellant strip coated with an active insect control ingredient and constructed with an untextured surface in accordance with the present invention.
Figure 1K:
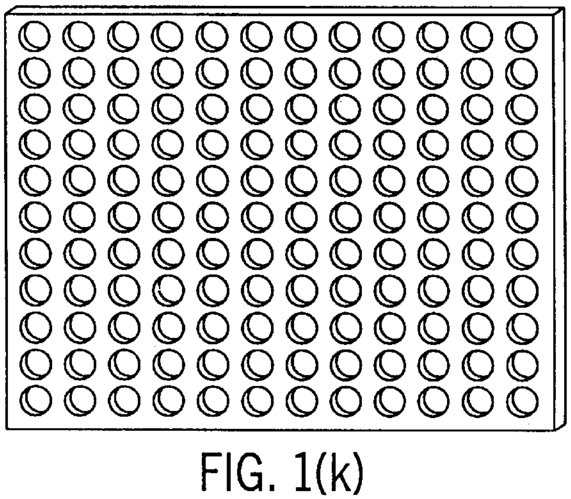

As used in this specification, "insect control" of flying insects is defined as at least repelling and preferably rendering the flying insects moribund. "Passive evaporation" is the process by which an active insect control ingredient evaporates from a substrate into the atmosphere through molecular separation, without the application of external thermal energy to the substrate, whether by burning the substrate, use of a heating element, or other means. "Molecular separation" shall be deemed achieved if particles of an active insect control ingredient cannot be detected by conventional light scattering counter techniques using an instrument such as the Climet Model CI-7300 Light Scattering Counter, made by Climet Instruments Company of Redlands, Calif. This instrument is capable of detecting airborne particles as small as 0.3 microns. "Effective amount" shall mean an amount sufficient to attain the desired purpose of at least repelling but preferably rendering flying insects moribund. A substrate shall be deemed to be "impregnated" with an active insect control ingredient if that ingredient is generally distributed either partially or completely within the material of the substrate in such a manner that the ingredient is directly held within the substrate and is supported thereby. A material is deemed to be "absorbing" if the active penetrates into the micropores of the material and is held therein by capillary forces. A substrate shall be deemed to be "coated" with an active insect control ingredient if that ingredient is generally distributed directly on the surface of the substrate in such a manner that the ingredient provides a layer on the substrate and is supported thereby. An ingredient held within or borne by intervening carriers or delayed-release means such as microcapsules, particles primarily composed of materials other than the ingredient, plastic materials, or the like that are then distributed within a substrate shall not be considered to be "directly" held within or on the substrate. "Non-absorbing" material shall be understood to describe materials where the solubility of the active in the substrate is less than 40 $\mu g/cm^2$. "Solubility" as used herein refers to the weight gain of a substrate due to absorption of the active by the substrate material when the active is kept in direct contact with the substrate for 14 days at 25° C.

As used in this specification, a material is "inert" with respect to another material if it (a) does not chemically react with that material, (b) it is not dissolved by that material, or (c) it does not solubilize that material.

The insect control article to control flying insects of the present invention falls within the class of insect control articles that include a substrate coated with an effective amount of an active insect control ingredient available for passive evaporation from the substrate. The substrate of the invention may be made of any material capable first of receiving and holding an active insect control ingredient and then of releasing it by passive evaporation. Suitable materials include, without limitation, structures molded of non-absorbing plastics. The preferred plastic film is an acrylonitrile methacrylate copolymer available under the trademark "Barex" from BP Chemicals, but other non-absorbing polymeric films such as polyester (PE), polyvinylidene chloride e.g. Saran (PVDC), orientated high density polethylene (orientated HDPE), nylon, polyvinyl alcohol (PVOH), orientated polypropylene (OPP), and ethylene vinyl alcohol (EVOH) films may also be used as the substrate material.

As is noted in the discussion above, the art teaches the use of various insecticides for passive evaporation for the control of insects, for the most part although not exclusively in drawers, closets, tents, and other very limited spaces or as insecticidal barriers intended to affect insects in close proximity to a treated carrier strip or the like. This teaching of the art would lead one to expect equally successful flying insect control from the passive evaporation of pyrethrum, sometimes microencapsulated (e.g. Landsman, Clarke, Whitcomb, Chadwick et al), pyrethroids in general (e.g. generic references in Ensing, Ronning, et al, and elsewhere), and particular pyrethroids, such as permethrin (Samson et al, U.S. Pat. No. 5,189,287), vaporthrin, permethrin, bioresmethrin, bioallethrin, kadethrin, decis, cyfluthrin, and fenfluthrin (Kauth et al) and permethrin, deltamethrin, cyhalothrin, and cypermethrin (Chadwick et al). These examples are intended to be illustrative and not exhaustive.

To the limited extent that the art is suggestive or predictive of success, all of these insecticides would appear equally attractive, along with apparently equally attractive non-pyrethroid insecticides (Whitcomb, Clarke, etc.). However, in research discussed below, the present inventors have found that in fact, with the exception of transfluthrin, and tefluthrin, the examples of these actives that were tested were not sufficiently effective to be employed successfully for the practical control of mosquitoes, for example, in a space as large as a typical sleeping room or in the open area of a patio without also employing mechanical devices such as fans or heaters to disperse the active.

"Practical control" shall mean a level of control comparable to that of a conventional mosquito coil which has been found to correspond to a transfluthrin release rate of 0.2 mg/hr.

It has now been discovered that unexpected and favorable results are achieved in the practical control of flying insects when the active insect control ingredient used in the insect control article of the invention is selected from the group consisting of the transfluthrin, tefluthrin, and combinations thereof. To most easily achieve the practical control standard, it is preferred that the active insect control ingredient include at least one of transfluthrin and tefluthrin. Of those two, transfluthrin is preferred as less irritating and otherwise objectionable for use in the presence of humans.

The particular active insect control ingredients disclosed now have been found to be sufficiently effective as insect control active ingredients that their airborne concentration is sufficient to achieve control of flying insects and, in particular, of mosquitoes and flies, when these ingredients are delivered by passive evaporation into the air when the substrate of the invention is placed in an environment with non-augmented air movement at air temperatures between 10° C. and 45° C. At the same time, these selected materials'vapor pressures at those temperatures are low enough that it is practical and economical to use them as active ingredients on substrates of a convenient size in amounts sufficient to achieve such insect controlling concentrations over time periods long enough to be sufficient to protect a room overnight or even for a series of nights. A useful commercial goal is to achieve protection for at least thirty consecutive nights of use. By use of the active ingredients of the invention, this goal is within practical reach.

Any effective conventional method may be used to coat the substrate with the active insect control ingredient. Typically, the substrate is coated with the active insect control ingredient by dissolving an appropriate amount of the active insect control ingredient in a solvent, thoroughly wetting the substrate with the solvent, and then drying the substrate to evaporate the solvent contained in the substrate and leave the substrate coated with the active insect control ingredient. The total release rate of a non-absorbing substrate coated with active depends directly on the area available for evaporation. The amount of active insect control ingredient per square centimeter of substrate necessary to be effective to control flying insects in an insect control article of the invention will depend upon the longevity of controlled release desired. Preferably, the active insect control ingredient is present approximately in an amount not less than 1 $\mu g/cm^2$ and preferably from 1–320 $\mu g$ per square centimeter of macro surface area. For the purpose of this discussion, "macro surface area" means the surface area as measured with a ruler or similar device. The preferred amounts of the active insect control ingredients identified above per square centimeter of macro surface area can be used on a substrate of a size convenient to handle and otherwise deal with when substantial insect control within a typical sleeping room, for example, is to be achieved for from 3 to 1080 hours (equivalent to 90 days of 12 hour per day operation) by hanging or placing the substrate in the room. The substrate may be in any shape such as a strip, disc, square, rectangle, parallelogram, expandable (e.g. accordion shaped), etc. As shown in FIGS. 1(*a*) through 1(*m*) the substrate may have an untextured surface (FIG. 1(*a*)), a surface with capillary grooves (FIG. 1(*b*)), a mesh surface (FIG. 1(*c*)), a textured surface (FIG. 1(*d*)), or a reticulated surface with capillary grooves on the inside surfaces of the openings in the substrate (FIGS. 1(*e*) and 1(*f*)), with texture on the inside surfaces of the openings in the substrate (FIGS. 1(*g*) and 1(*h*)), with texture on both the outside surface of the substrate and the inside surfaces of the openings in the substrate (FIGS. 1(*i*) and 1(*j*), without either texture or capillary grooves (FIG. 1(*k*)), or with capillary grooves on both the outside surface of the substrate and the inside surfaces of the openings in the substrate (FIGS. 1(*l*) and 1(*m*)). As noted herein each substrate illustrated is composed of a material that is non-absorptive and inert. However, the invention is not limited to these precise sizes and shapes.

The insect control article of the present invention can be placed in any environment where there is non-augmented air movement that will pass over the coated substrate, thereby allowing the active insect control ingredient to continuously passively evaporate into the atmosphere for an extended period of time. Suitable environments include enclosed rooms as well as volumes of open air space, such as patios, and the like, with air movement provided by natural air movement.

In one embodiment of the present invention, the insect control article includes hanger means for suspending the coated substrate in a suitable environment provided with non-augmented air movement to allow the active insect control ingredient to passively evaporate into the atmosphere. Examples of suitable hanger or attachment means include hooks, strings, magnetic clips, clamps, velcro, mechanical clips and fasteners, adhesives, and the like. Any such means provided on the substrate should not substantially block the passage of air over the substrate.

The method of the invention for controlling flying insects includes, as a first step, providing an insect control article to control flying insects that includes a non-absorptive and inert substrate that is coated with an active insect control ingredient selected from the group consisting of transfluthrin, tefluthrin, and combinations thereof in an amount of less than or equal to 40 $\mu g/cm^2$ of substrate macro surface area. The insect control article is then placed in an environment with non-augmented air movement, and the substrate of the insect control article is exposed to the air. The active insect control ingredient with which the substrate is coated is then allowed to passively evaporate into the air.

One aspect that differentiates the present passive space repellent concept from other continuous action products is that the release rates from continuous action products like liquid vaporizers, mosquito coils, electric mats and the like are more or less independent of the surrounding environment. This is so because the driving force for discharge of the active is supplied from within the system. For a passively evaporating space repellent product, the release rate depends strongly on the surrounding environment. The driving force for evaporation of the active is primarily controlled by the environmental factors such as the velocity of air flowing past the repellent strip, ambient temperature, concentration build-up of the active in the vicinity of the product, and air exchange rate. Product robustness, as a consequence, becomes extremely difficult since the consumer expects the product to work in all different climates around the world.

The efficacy of a passive space repellency based product in a large room essentially depends on the release rate of the active in adequate quantities. Hence developing this technology principally lies in identifying suitable actives and just as importantly in identifying the factors that govern the release rates of the active. Some of the key issues that are addressed hereinafter are:

1. Identify insecticidal actives that can be released via evaporation at room temperature that are sufficiently efficacious in repelling flying insects.
2. Determine effect of substrate material on release rates and identify those that give enhanced overall release rates.
3. Determine release rate profiles and check if the release rates are constant over time for different types of substrate materials.
4. Determine the effect of solvent on release of transfluthrin and identify those that increase release rates.
5. Determine the effect of dose level on the product efficacy and estimate range for product life (overnight vs. seven day product etc).

The following non-limiting examples demonstrate the insect control article and method of the invention. The invention should not be understood as being limited to these particular examples, which are only illustrative.

EXAMPLE 1

Experimental Methodologies

Strips of various materials were coated using an intermediate solution of the active. These strips were tested in a wind tunnel for evaporation losses and in a glass chamber for knockdown efficacy. Analytical tools were used to determine residual levels on the strips.

(a) Preparation of Coated Strips

Strips 2 inches by 10 inches in size were cut from substrate films 10 as shown in FIG. 1. Markings were made to identify the side to be treated with the active. Markings were also made to leave one inch spacing on either ends 12 and 14 of the strip 10 to enable handling. Intermediate solutions of the active in organic solvents were prepared. A micropipettor, calibrated to transfer a known amount of intermediate solution on to the strip, was used to dose the strip with the active. The solution, after transferring onto the strip 10, was made to wet a 2 inch by 8 inch area 16 between ends 12 and 14, and allowed to sit on the bench top until most of the solvent evaporated and the strips appeared dry (which took 15 minutes to 30 minutes). Strips 10 were then either folded twice and held together with a metal clip and kept in a glass jar or were wrapped in aluminum foil and kept in a sealed plastic bag. These were then stored in the refrigerator at −10° C. until further use.

(b) Release of Active in Wind Tunnel

Figure 2:
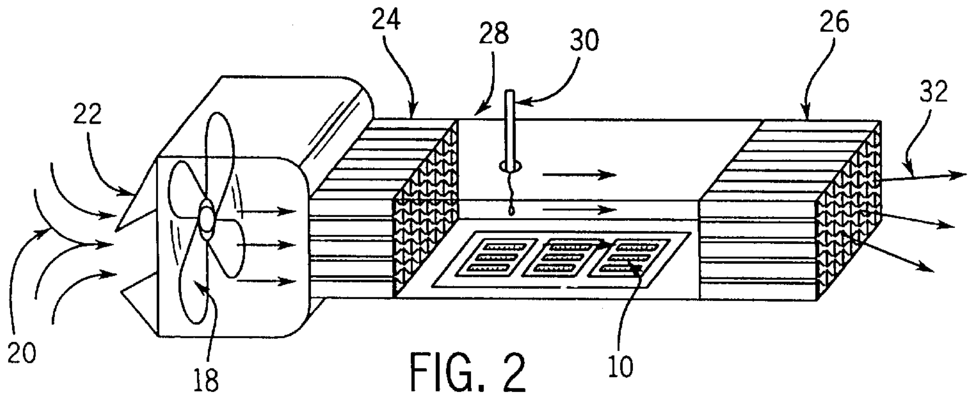
FIG. 2 is a schematic illustration of a computer controlled wind tunnel for determining the release of actives from the strips of FIGS. 1(*a*)–1(*m*)
Figure 1B:
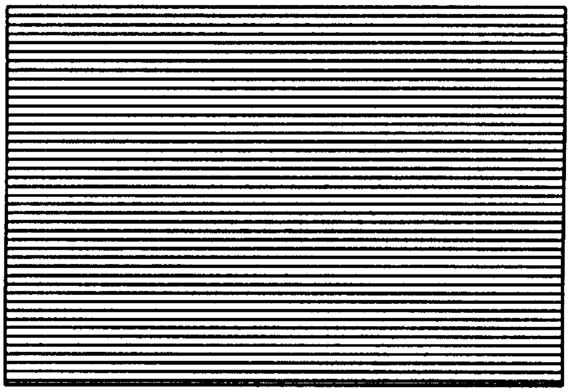
Figure 1C:
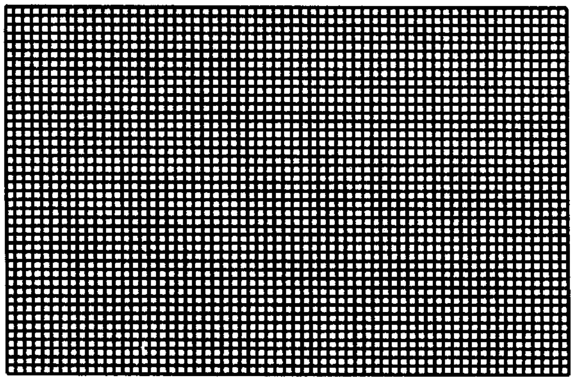
Figure 1D:
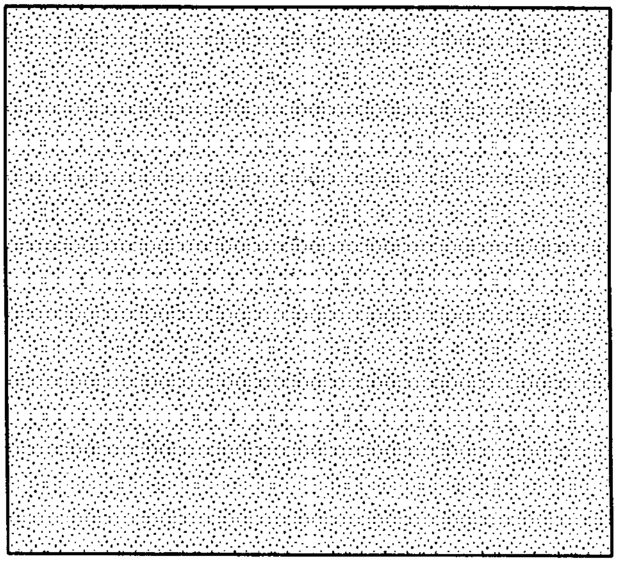
Figure 1E:
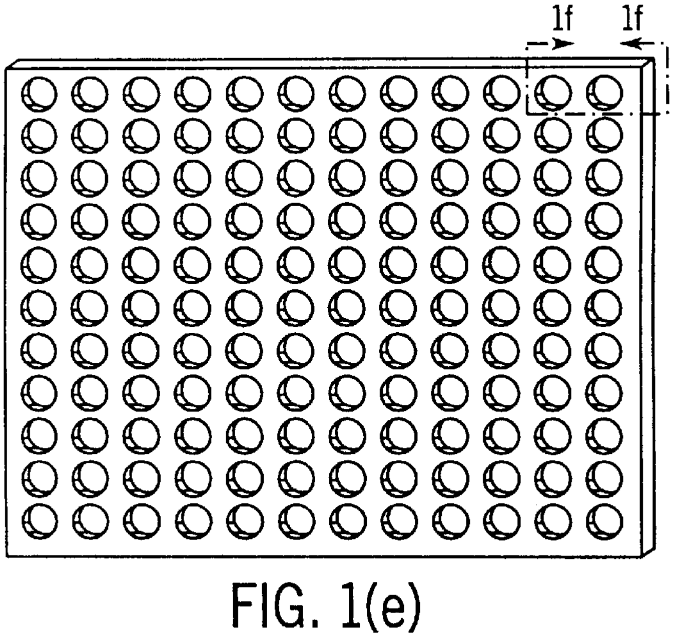
Figure 1F:
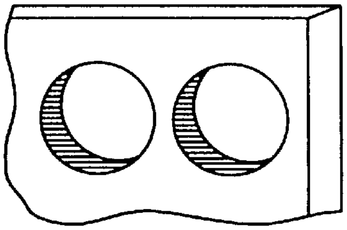
Figure 1G:
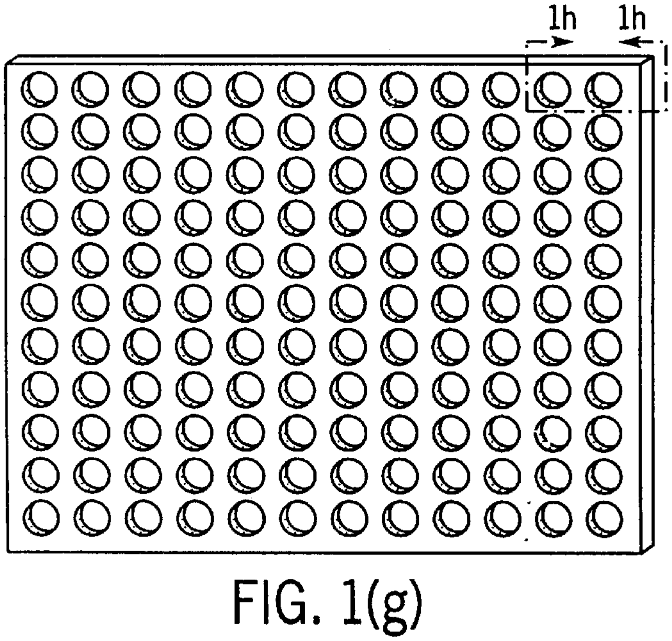
Figure 1H:
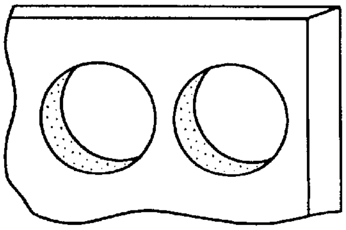
Figure 1I:
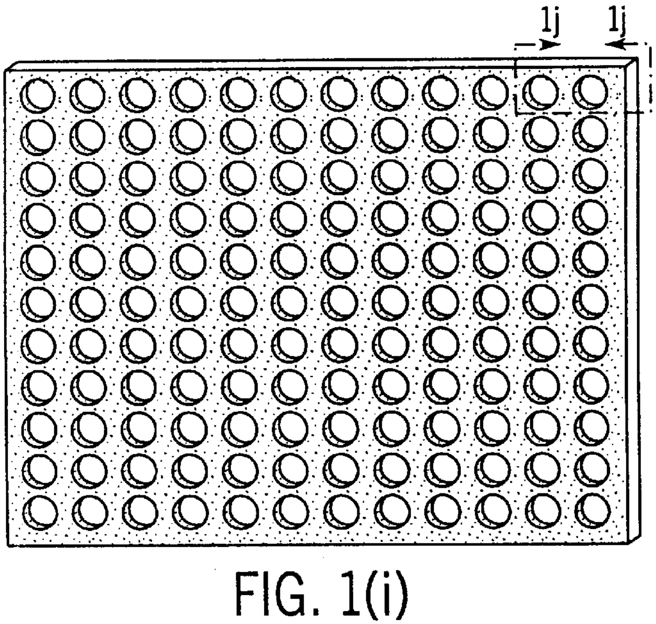
Figure 1J:
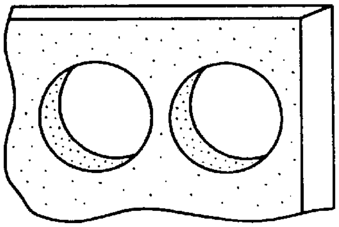
Figure 1L:
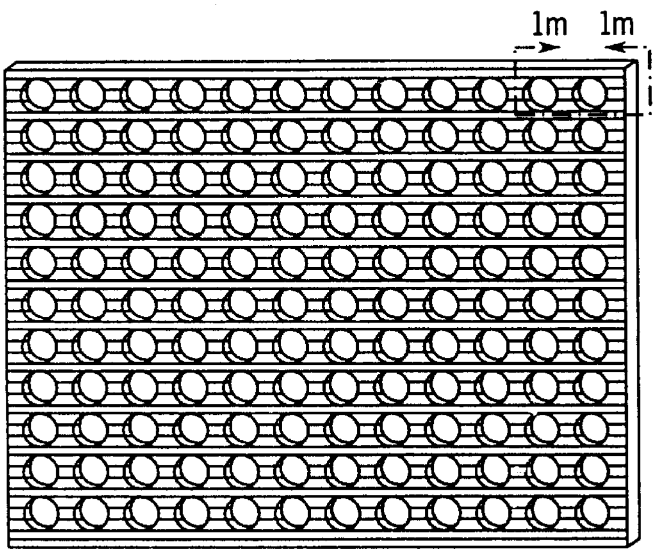
Figure 1M:
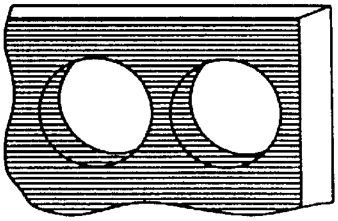

A computer controlled wind tunnel was custom designed using a fan 18 for drawing fresh air designated by arrows 20 past baffles 22 into a chamber 28 containing multiple strips 10 to determine the release of actives from these strips under controlled environmental conditions (see FIG. 2).

Preset wind velocities can be entered into the computer and maintained without operator's involvement during the testing period. Honey comb flow straighteners 24 and 26 were placed on either ends of the wind tunnel to obtain uniform velocity profiles. Strips 10 were placed on the floor of a 12 inch by 12 inch cross sectioned body in triplicates in a staggered fashion so as to equalize any possible errors that arise from spatial dependency of air velocity. All studies were carried out at a constant air flow rate of 2 meters per second as determined by a velocity probe 30 in chamber 28 and at an ambient temperature of 70° F. for 72 hours. The exhaust designated by arrows 32 of the wind tunnel was directly connected to the building ventilation duct to prevent Transfluthrin contamination of the lab. Strips 10 were removed at predetermined intervals and stored in the refrigerator for subsequent analytical or biological testing.

(c) Knockdown Efficacy Against Mosquitoes in Glass Chamber

A Glass chamber (0.75 m×0.75 m×0.75 m) was used for the test and was maintained at 80° F. and 50% relative humidity. Three treated strips were placed on a card board tray covered with an aluminum foil and then transferred to the glass chamber. The strips were exposed in the chamber for three minutes to allow insecticide vapors build-up in the enclosed air. Strips were then quickly removed, folded and stored in the refrigerator. Ten laboratory-cultured adult Aedes Aegypti female mosquitoes were released into the chamber. Knockdown of mosquitoes were observed at indicated intervals up to 20 minutes. After 20 minutes of exposure, all mosquitoes were collected and placed in a container with sucrose pad. Mortality value was observed at 24 hours post treatment. KD50, KD80, and % Dead values of the tests were obtained for analysis. KD50 and KD80 are defined as the time taken for 50% and 80% of the mosquitoes to get knocked down and % Dead is simply the percentage of mosquitoes that are dead after 24 hour period. The glass chamber was then dismantled and thoroughly wiped with soap solution to remove contamination of the active. The walls were then wiped with a paper towel and allowed to dry before assembling again for the next run.

To validate the use of above glass chamber method towards testing efficacy of repellent strips, a dose response study was conducted with different number of Barex strips, each coated in an identical fashion with 5 mg of transfluthrin. Results as shown in Table 1 suggest that KD50 and KD80 show an excellent response to the number of strips and hence the total release of transfluthrin thus validating the use of glass chamber for biological testing.

TABLE 1

Effect of strip area on biological response

| No. of Strips | Dead (%) | KD50 (min) | KD80 (min) |
|---|---|---|---|
| 1 Barex strip | 0 | 20.0 | 20.0 |
| 2 Barex strip | 100 | 13.3 | 15.0 |
| 4 Barex strip | 100 | 6.5 | 9.0 |
| 7 Barex strip | 80 | 5.0 | 6.3 |
| 10 Barex strip | 100 | 3.8 | 4.5 |

(d) Residual Analysis

A validated analytical method was used to determine the residual level of active on the strips using gas chromatography. All samples were analyzed using this method to determine evaporation losses and release rates in the wind tunnel.

EXAMPLE 2

Effect of IC Actives

Nineteen different insecticidal actives were tested in the glass chamber for knockdown efficacy to identify possible candidates for the present spatial repellent strip technology. Barex strips were coated with 5 mg of each of these actives by micropipetting 2% intermediate solutions. These intermediate solutions were prepared using Isopar E as the solvent for all actives except for bioallethrin, natural pyrethrum, propoxur, and deltamethrin which were found to be forming precipitates in Isopar E. In these cases, isopropyl alcohol (IPA) was used as solvent for the first three actives and toluene for the fourth one. The strips were tested in glass chamber for knockdown efficacy. The results are shown in Table 2. Only transfluthrin and tefluthrin showed any knockdown activity during the 20 min. test period. While transfluthrin showed highest activity and has a KD50 value of 4.6 min, tefluthrin displayed relatively lower activity and has a KD50 value of 13 min. The remaining actives (Etoc, EBT, PF, Sumithrin, New Neo-PF, Cypermethrin Tech., Bioallethrin, Dursban, Fenvalerate, Eucalyptus, DEET, Citronella Oil, Permanone Tech., Resmethrin, Natural Pyrethrum, Deltamethrin, Propoxur, and Vaporthrin) showed either minimal activity or no activity at all during the 20 minute test period.

TABLE 2

Effect of IC actives on biological response

| Active | Dead (%) | KD50 (min) | KD80 (min) |
|---|---|---|---|
| ETOC | 0 | >20 | >20 |
| EBT | 0 | >20 | >20 |
| PF | 0 | >20 | >20 |
| Sumithrin | 0 | >20 | >20 |
| New Neo-PF | 0 | >20 | >20 |
| Tefluthrin | 100 | 13.00 | 16.67 |
| Cypermethrin | 0 | >20 | >20 |
| Bioallethrin | 0 | >20 | >20 |
| Dursban | 0 | >20 | >20 |
| Fenvalerate | 0 | >20 | >20 |
| Eucalyptus | 0 | >20 | >20 |
| DEET | 0 | >20 | >20 |
| Citronella | 0 | >20 | >20 |
| Permanone | 0 | >20 | >20 |
| Resmethrin | 10 | >20 | >20 |
| Natural Pyrethrum | 0 | >20 | >20 |
| Deltamethrin | 20 | >20 | >20 |
| Vapothrin | 0 | >20 | >20 |
| Transfluthrin | 100 | 4.58 | 6.83 |

Since the active level was only 5 mg, it is possible that relatively more volatile actives such as eucalyptus may have evaporated from the strip completely even before the strip was exposed in the glass chamber.

EXAMPLE 3

Effect of Substrate Material

In an attempt to investigate less expensive but equally efficacious material, a number of substrates, namely, plastic films, cellulose and glass fiber filter papers, and nonwovens, were obtained and tested in the wind tunnel and glass chamber to determine their effect on the release rates of transfluthrin. The objective was to identify parameters that lead to superior performance and seek and obtain new substrate materials that were less expensive and easily available.

(a) Ideal Substrates

Two idealized substrates, namely a sheet of aluminum foil and a glass surface were tested in the glass chamber together with Barex. Results are shown in Table 3 where Barex appears to be one of the best substrates for effectively releasing transfluthrin under ambient conditions.

TABLE 3

Biological response of aluminum, glass, and Barex substrates in glass chamber.

| Substrate Material | Dead (%) | KD50 (min) | KD80 (min) |
|---|---|---|---|
| Aluminum Foil | 60 | 6.00 | 8.00 |
| Glass surface | 100 | 4.25 | 5.00 |
| Barex | 100 | 4.6 | 6.8 |

(b) Plastic Substrates

Fifteen different commercial plastic film samples were obtained from BP, Allied, DuPont, Exxon, Dow, Mobil, Tredegar, Huntsman, and Kururay. Strips of these samples were coated with 5 mg transfluthrin using Isopar E solvent as described in Example 1, Section (a) and exposed in the wind tunnel of FIG. 2 for spontaneous evaporation of the active into the flowing air as described in Example 1, Section (b). Samples were then evaluated for residual losses to determine total amount of active evaporated. Performance of all substrates is presented in Table 4.

TABLE 4

Effect of plastic material on release of Transfluthrin

| Product Name | Film Type | Coated side | Manu-facturer | Caliper (mil) | % evapo-rated | Release Index wrt. Barex Substrate |
|---|---|---|---|---|---|---|
| Mylar | PET | PET | DuPont | 2 | 77.8 | 1.01 |
| Barex | Acrylonitrile Methacrylate copolymer | Barex | BP | 2 | 77.1 | 1.00 |
| Monax HD-A | Oriented HDPE | HDPE | Tredegar | 1 | 74.9 | 0.97 |
| M34 | PET with Saran (PVDC) coating | PVDC side | DuPont | 0.5 | 74.9 | 0.97 |
| Capran-Emblem 2500 | Nylon Film | Nylon | Allied | 1 | 71.9 | 0.93 |
| Bicor 84AOH | OPP, one side PVOH and one side acrylic | PVOH side | Mobil | 0.84 | 71.9 | 0.93 |
| Eval EF-F | EVOH film | EVOH | Kururay | 0.6 | 71.2 | 0.92 |
| Extrel 15 | Polypro-pylene Copolymer treated on one side | Treated side | Exxon | 3 | 50.5 | 0.65 |
| LDPE | LDPE | LDPE | Dow Plastics | 2 | 41.6 | 0.54 |
| Extrel 15 | Polypro-pylene Copolymer treated on one side | PP | Exxon | 3 | 41.6 | 0.54 |
| LMAX-200-1 (LOW SLIP) | LLDPE treated on one side | LLDPE side | Huntsman | 3 | 33.5 | 0.43 |
| Lio-20 | Surlyn treated one side | Surlyn treated side | Huntsman | 2 | 33.5 | 0.43 |
| LMAX-200-1 (Low Slip) | LLDPE treated on one side | LLDPE treated side | Huntsman | 3 | 30.5 | 0.40 |
| Lio-20 | Surlyn treated one side | Surlyn side | Huntsman | 2 | 26.8 | 0.35 |

While the evaporation rates lie between 26.8% and 77.8%, these numbers could be lower or higher depending on the exposure time and velocity of blowing air in the wind tunnel. However, the relative magnitudes are more important than anything else since this indicates how well the substrate is able to release the active under similar conditions.

It will be demonstrated in Example 4 that release rates are uniform until all the active is released and hence release rates are proportional to "% evaporated". The evaporation losses were therefore expressed in terms of "release index" in Table 4 where the evaporation losses for all plastics are normalized with that of Barex material. While the "% evaporated" is a function of air flow rate and exposure time, the "release index" depends only on how well the substrate releases the active relative to Barex material under constant environmental conditions. The higher the "release index", the better is the substrate's ability to release the active. Since Barex is considered as close to an idealized substrate, all substrates with release indices close to unity would be most suitable for as substrates for passive evaporation technology. Results indicated that in addition to Barex, which is an acrylonitrile methacrylate copolymer, substrates composed of polyester (PE), polyethylene terephthalate (PET), oriented high density polyethylene (HDPE), polyvinylidene chloride (PVDC), nylon, orientated polypropylene (OPP), polyvinyl alcohol (PVOH), and ethylene-vinyl alcohol copolymers (EVOH) are excellent materials in releasing transfluthrin and that the release rates from these polymeric materials are as good as idealized substrate Barex.

A study was carried out in an attempt to identify a general class of substrate materials that provide highest release rate of transfluthrin. The objective was to distinguish parameters that determine evaporation of transfluthrin from these materials. It was found that the solubility of transfluthrin correlates well with its evaporation from plastics. The lower the solubility, the higher is the overall release rate. Fifteen different plastics were coated with 75 mg of transfluthrin on a 103 sq. cm. area using a 25% active intermediate. Controls for each of these plastics were also prepared by coating strips with Isopar E solvent only. During application, wettability characteristics of Isopar E and transfluthrin on the strip before and after the evaporation of solvent was noted. All samples were preweighed before coating. Samples were dried for 20 hours, folded together and stored in a sealed glass jar at 25° C. for 14 days. Samples were then removed and wiped thoroughly with Isopar E using lint free Accu-Wipe paper towels on both sides of the strips. These were then dried on each side for a total of 20 hours and weighed again to determine the amount of transfluthrin and solvent absorbed into each of the strips. In another separate experiment, surface energies of each of the plastic substrates were determined using Accu-Dyne-Test Marker Pens.

Based on the gravimetric data, the amount of transfluthrin absorbed into each of the plastic strips were determined by correcting for the change in weight due to the solvent alone. The data is shown in Table 5. Correlation coefficients were determined between parameters such as thickness of the film, weight of the strip, % evaporation of transfluthrin, total absorption of transfluthrin, absorption of transfluthrin per unit film thickness, absorption of transfluthrin per unit weight, % absorption of transfluthrin with respect to (wrt) weight of the strip, and surface energy of the strip (see Table 6) to reduce the number of variables in data analysis.

Figure 3:
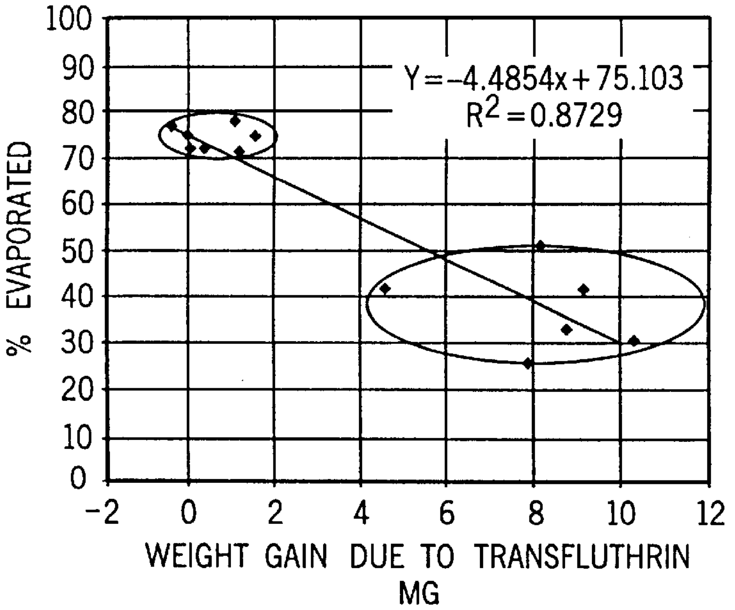
FIG. 3 is a graph illustrating the percent evaporation versus solubility of transfluthrin in plastics.

Results indicate that the response variable "%evaporated" is strongly correlated to the total amount of transfluthrin absorbed. The total amount of transfluthrin absorbed, in turn, is related to thickness of the film and to some extent, to the surface energy of the strip. Multiple linear regression analysis suggested that the fit is best if "%evaporated" is regressed on "Wt. gain due to transfluthrin only". A plot of these two variables is shown in FIG. 3.

TABLE 5

Solubility of Transfluthrin in, and surface energy and wettability of various plastics

| Product Name | Film Type | Coated Side | Manufacturer | Caliper (mil) | Surface Energy (dyne/cm) | Avg. Strip Weight (mg) | Wt. gain due to Transluthrin and solvent (mg) |
|---|---|---|---|---|---|---|---|
| Barex | Acrylonitnie Methacrylate copolymer | Barex | BP | 2 | 60 | 750.08 | −1.1 |
| Capran-Embiem 2500 | Nylon Film | Nylon | Allied | 1 | 58 | 376.29 | −1.43 |
| Mylar | Pet | PET | DuPont | 2 | 42 | 987.90 | 0.14 |
| Monax HD-A | Oriented HDPE | HDPE | Tredegar | 1 | 42 | 385.72 | 1.96 |
| Extrel 15 | Poly-propylene Copolymer treated on one side | Treated side | Exxon | 3 | 35 | 880.71 | 8.74 |
| LMAX-200-1 (LOW SLIP) | LLDPE treated on one side | LLDPE side | Huntsman | 3 | 33 | 931.18 | 8.74 |
| LMAX-200-1 (LOW SLIP) | LLDPE treated on one side | LLDPE treated side | Huntsman | 3 | 41 | 924.59 | 10.04 |
| LDPE | LDPE | LDPE | Dow Plastics | 2 | 33 | 667.09 | 4.91 |
| M34 | PET with Saran (PVDC) coating | PVDC side | DuPont | 0.5 | 35 | 240.63 | 0.07 |
| Eval EF-F | EVOH film | EVOH | Kururay | 0.6 | 58 | 185.03 | −0.62 |
| Bicor 84AOH | OPP, one side PVOH and one side acrylic | PVOH side | Mobil | 0.84 | >60 | 260.87 | 0.09 |
| Bicor 8AOH | OPP, one side PVOH and one side acrylic | Acrylic side | Mobil | 0.84 | 52 | 259.28 | −8.28 |
| Extrel 15 | Poly-propylene Copolymer treated on one side | PP | Exxon | 3 | <30 | 900.10 | 9.73 |
| Lio-20 | Surlyn treated one side | Surlyn side | Huntsman | 2 | 42 | 583.95 | 8.33 |
| Lio-20 | Surlyn treated one side | Surlyn treated side | Huntsman | 2 | 36 | 581.35 | 9.4 |

| Product Name | Film Type | Wt. gain due to Solvent (mg) | Wt. gain due to Transfluthrin Only (mg) | Wt. gain per mil (mg/mil) | % Wt. gain (wrt.* strip wt) | % evaporated | Wetting of Transfluthrin | Wetting of Solvent |
|---|---|---|---|---|---|---|---|---|
| Barex | Acrylonitnie Methacrylate copolymer | −0.66 | −0.44 | −0.22 | −0.0587 | 77 | Good | Good |
| Capran-Embiem 2500 | Nylon Film | −1.4 | −0.03 | −0.0.3 | −0.0080 | 72 | Good | Good |
| Mylar | Pet | −0.92 | 1.06 | 0.53 | 0.1073 | 78 | Good | Good |
| Monax HD-A | Oriented HDPE | 0.43 | 1.53 | 1.53 | 0.3967 | 75 | Good | Good |
| Extrel 15 | Poly-propylene Copolymer treated on one side | 0.54 | 8.2 | 2.73 | 0.9311 | 50 | Good | Good |
| LMAX-200-1 (LOW SLIP) | LLDPE treated on one side | 0.09 | 8.65 | 2.88 | 0.9289 | 33 | Bad | Good |
| LMAX-200-1 (LOW SLIP) | LLDPE treated on one side | −0.28 | 10.32 | 3.44 | 1.1162 | 31 | Good | Good |

TABLE 5-continued

Solubility of Transfluthrin in, and surface energy and wettability of various plastics

| | | | | | | | | |
|---|---|---|---|---|---|---|---|---|
| LDPE | LDPE | 0.38 | 4.53 | 2.27 | 0.6791 | 42 | Bad | Good |
| M34 | PET with Saran (PVDC) coating | 0.14 | −0.07 | −0.14 | −0.0291 | 75 | Good | Good |
| Eval EF-F | EVOH film | −1.78 | 1.16 | 1.93 | 0.6269 | 71 | Good | Good |
| Bicor 84AOH | OPP, one side PVOH and one side acrylic | −0.21 | 0.3 | 0.36 | 0.1150 | 72 | Good | Good |
| Bicor 8AOH | OPP, one side PVOH and one side acrylic | −0.12 | −8.16 | −9.71 | −3.1472 | 56 | Good | Good |
| Extrel 15 | Poly-propylene Copolymer treated on one side | 0.59 | 9.14 | 3.05 | 1.0154 | 42 | Bad | Good |
| Lio-20 | Surlyn treated one side | 0.45 | 7.88 | 3.94 | 1.3494 | 27 | Bad | Good |
| Lio-20 | Surlyn treated one side | .063 | 8.77 | 4.38 | 1.5086 | 33 | Bad | Good |

*The abbreviation “wrt” means “with respect to.”

TABLE 6

Correlation coefficients between response and predictor variables

| | Caliper (mil) | Surface energy (dyne/cm) | Avg. Strip Weight | Wt. gain due to Transfluthrin Only (mg) | Wt. gain per mil | % Wt. gain (wrt. strip st) | % evaporated |
|---|---|---|---|---|---|---|---|
| Caliper | 1.000 | | | | | | |
| Surface Energy (dyne/cm) | −0.565 | 1.000 | | | | | |
| Avg. Strip Weight | 0.930 | −0.505 | 1.000 | | | | |
| Wt. gain due to Transfluthrin Only (mg) | 0.822 | −0.673 | 0.612 | 1.000 | | | |
| Wt. gain per mil | 0.606 | −0.574 | 0.381 | 0.919 | 1.000 | | |
| % Wt. gain (wrt. strip wt) | 0.601 | −0.554 | 0.366 | 0.919 | 0.997 | 1.000 | |
| % evaporated | −0.701 | 0.601 | −0.477 | −0.934 | −0.907 | −0.911 | 1.000 |

This suggests that the solubility of the pesticide in the substrate is the determining factor for its subsequent release into the ambient. Surprisingly, surface energy of the plastic does not appear to play a critical role in this phenomenon. Substrates with transfluthrin solubility of <2 mg/strip (20 $\mu g/cm^2$) appear to show the best release rates and substrates with transfluthrin solubility of >4 mg/strip (=40 $\mu g/cm^2$) does not release transfluthrin efficiently. Although this conclusion is strictly valid when the strips are coated with 5 mg of transfluthrin in determining the “% evaporated” values, it should be generally true that substrates that have low transfluthrin solubility perform better in terms of releasing the active especially when the active level is <5 mg per strip. The lower the active level, the more prominent will be the substrate effect on the release of transfluthrin i.e., the differences in release rates would be a much stronger function of the solubility. When the active level is ≧5 mg per strip, the “% evap.” values become closer to each other and would eventually merge into a single value at very high dose levels when the substrates are thin. At very high dose levels or coating densities, the solubility would have negligible effect on the release rates at least until most of the applied transfluthrin vaporizes from thin substrates. When the substrates are very thick, even at high dose levels, the release rates would depend on the solubility of the active in the plastic material. This is because the thick plastic sheet is now capable of solubilizing a high level of transfluthrin comparable to the initial applied amount.

Thus, any non-absorbing material is suitable for using as the substrate for releasing insecticide in non-augmented air movement. For example, barrier materials such as glassy polymeric films, aluminum foils, glass surfaces etc., would have minimal solubility of active and hence would be the best substrates.

(c) Absorbing Substrates

To determine the effect of absorbing substrates on the efficacy, filter paper, glass fiber, aged glass fibers and nonwoven samples of varying degrees of porosities, pore sizes, and thicknesses, each coated with 5 mg of transfluthrin on a 103 sq. cm. surface area were tested in the glass chamber. Results indicated that fresh samples of glass fibers performed just as good as Barex while nonwovens performed worst. Cellulose based filter papers showed marginally lower performance compared to glass fibers possibly due to partial absorption of transfluthrin by cellulose (see Table 7 and 8).

TABLE 7

Biological efficacy of fresh filter paper substrates in glass chamber

| Product Name | Pore size | Thickness | Supplier | VWR Catalogue No. | Dead (%) | KD50 (min) | KD80 (min) |
|---|---|---|---|---|---|---|---|
| Grade 410 Filter Paper (Smooth) | 1 micron | 7.5 mil | VWR | 28297-830 | 60 | 7.00 | 9.25 |
| Grade 413 Filter Paper (Smooth) | 5 microns | 7.0 mil | VWR | 28310-208 | 90 | 5.50 | 7.00 |
| Filter Paper Type 2 (Smooth) | 8 microns | 7.5 mil | Whatman | 1002-240 | 100 | 6.50 | 7.00 |
| Grade 415 Filter Paper (Crepe) | 25 microns | 11 mil | VWR | 28320-223 | 100 | 7.00 | 7.50 |
| Grade 417 Filter Paper (Crepe) | 40 microns | 15 mil | VWR | 28313-181 | 70 | 7.09 | 9.27 |

TABLE 8

Biological efficacy of fresh glass fiber substrate in glass chamber

| Product Name | Pore size | Thickness | Supplier | Catalogue No. | Dead (%) | KD50 (min) | KD80 (min) |
|---|---|---|---|---|---|---|---|
| Type A/B Binder Free Glass Fiber Filter Paper | 1 micron | 26 mil | VWR | 28150-978 | 80 | 4.75 | 6.50 |
| Type A/C Binder Free Glass Fiber Filter Paper | 1 micron | 11 mil | VWR | 28150-984 | 90 | 5.00 | 6.50 |
| Type A/D Binder Free Glass Fiber Filter Paper | 3.1 micron | 27 mil | VWR | 28150-999 | 100 | 4.50 | 6.50 |

Attempts to evaluate aged glass fiber samples (see Table 9) revealed that performance is minimal (insufficient biological activity as indicated by high KD50 and KD80 values) suggesting that release rates decay with aging in wind tunnel. "Aged" samples refer to samples exposed in the wind tunnel for 72 hours at 21° C. in which the air is moving at a velocity of 2 meters/second.

TABLE 9

Biological efficacy of aged glass fiber substrates in glass chamber

| Product Name | Pore size | Thickness | Supplier | VWR Catalogue No. | Dead (%) | KD50 (min) | KD80 (min) |
|---|---|---|---|---|---|---|---|
| Type A/B Binder free glass fiber filter paper | 1 micron | 26 mil | VWR | 28150-978 | 0 | 20.00 | 20.00 |
| Type A/C Binder free glass fiber filter paper | 1 micron | 11 mil | VWR | 28150-984 | 10 | 20.00 | 20.00 |
| Type A/D Binder free glass fiber filter paper | 3.1 micron | 27 mil | VWR | 28150-999 | 60 | 15.00 | 18.75 |

Performance of fresh samples of porous substrates does not appear to be a strong function of either pore size or thickness. This may be true because transfluthrin residing at the upper most layer would be evaporating from the fresh samples and hence, the sub-structure does not provide any resistance to evaporation. Performance of aged samples, however, is expected to strongly depend on these parameters. Limitations on testing methods on aged samples did not allow quantification of these effects.

TABLE 10

Biological efficacy of nonwovens in glass chamber

| Product Name | Fiber Type | Fiber size | Resin type | Construction | Weight | Dead (%) | KD50 (min) | KD80 (min) |
|---|---|---|---|---|---|---|---|---|
| NP Poly 45 | Polyester | 6 DPF | PVA | Bonded needle punched | 3.2 OZ/Sq. Yd. | 0 | >20 | >20 |
| NP Poly (MF-100) | Polyester | 1.5 DPF | Acrylic | Bonded needle punched | 3 OZ/Sq. Yd. | 20 | >20 | >20 |
| NP Polypropylene | Polyolefin (PP) 0.4 OZ PP scrim | 3 DPF | N/A | Needle punched | 4 OZ/Sq. Yd. | 0 | >20 | >20 |
| H.L. Cotton | 90% unbleached cotton and 10% polyester | 6 DPF | PVA | Bonded needle punched | 3 OZ/Sq. Yd. | 70 | 16.67 | >20 |

Fresh, nonwoven materials did not show much biological activity in the glass chamber (see Table 10).

It can therefore be concluded that porous structures such as nonwoven fiber papers, plastic papers, cloth, corrugated papers, synthetic or natural porous materials, etc., are not suitable for efficiently releasing the active because the release rates are low and decrease with time. A considerable amount of active will be entrapped and wasted.

EXAMPLE 4

Release Rate Profiles

Figure 4:
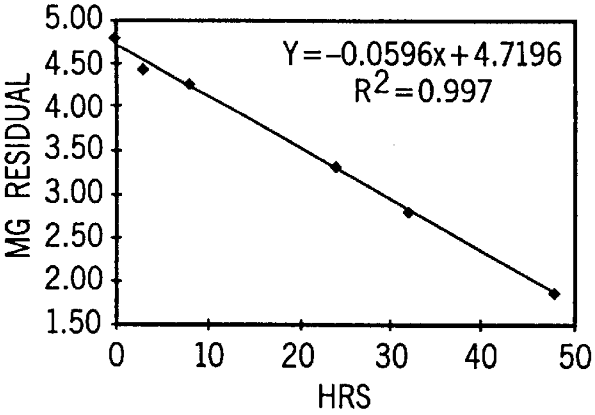
FIG. 4 is a graph illustrating the residual level of transfluthrin as a function of time from non-porous Barex strips.
Figure 5:
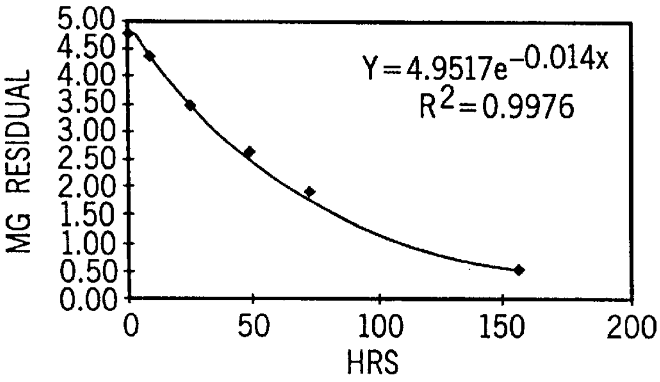
FIG. 5 is a graph illustrating the residual level of transfluthrin as a function of time from porous filter paper.

The objective of this study was to determine linearity of release of transfluthrin from an absorptive substrate and a non-absorptive and inert substrate. Filter paper and Barex strips coated with 5 mg of transfluthrin from Isopar E intermediate were subjected to evaporation in the wind tunnel of FIG. 2. The samples were removed at predetermined intervals and evaluated for residual levels. Experimentally determined release curves are shown in FIGS. 4 and 5. Release rates for Barex (FIG. 4) and filter paper (FIG. 5) strips were calculated from residual levels and are shown in Table 11.

TABLE 11

Release rates from Barex and filter paper

| Time | Barex | Filter paper |
|---|---|---|
| 0 hr | 0.58 $\mu$g/hr/cm$^2$ | 0.68 mg/cm$^2$/hr |
| 3 hr | 0.58 $\mu$g/hr/cm$^2$ | — |
| 8 hr | 0.58 $\mu$g/hr/cm$^2$ | 0.58 mg/cm$^2$/hr |
| 24 hr | 0.58 $\mu$g/hr/cm$^2$ | 0.48 mg/cm$^2$/hr |
| 32 hr | 0.58 $\mu$g/hr/cm$^2$ | — |
| 48 hr | 0.58 $\mu$g/hr/cm$^2$ | 0.38 mg/cm$^2$/hr |
| 72 hr | — | 0.29 mg/cm$^2$/hr |
| 156 hr | — | 0.10 mg/cm$^2$/hr |

Release rate of transfluthrin from Barex strips coated with a density of 48 $\mu$g/cm$^2$ remains highly uniform under the conditions tested while that of filter paper decreases exponentially with time. The advantage of using a non-absorptive and inert substrate such as Barex over that of an absorptive substrate such as filter paper is a consistently uniform performance over the entire product life. This eliminates residual loses and ensures optimal use of the active.

EXAMPLE 5

Effect of Solvent

Two different substrate materials, namely, Barex (a non-absorptive and inert substrate material) and filter paper (an absorptive material), and fifteen organic solvents based on differences in volatility and Hansen's three dimensional solubility parameters (Hansen D being the dispersive component, Hansen P being the polar component, and Hansen H being the hydrogen bonding component) were selected to determine the effect of solvent on the release of transfluthrin from porous and nonporous substrates. Strips of Barex and filter paper of 103 sq. cm. size were coated with 5 mg of transfluthrin and were subjected to evaporation in the wind tunnel of FIG. 2 and biological studies in the glass chamber.

TABLE 12

Effect of solvent on release of transfluthrin

| Solvent | VP (mm) | Hansen D | Hansen P | Hansen H | % Evap Filter Paper | % Evap Barex |
|---|---|---|---|---|---|---|
| Acetone | 185.0 | 7.6 | 5.1 | 3.4 | 57.7 | 58.3 |
| THF | 143.0 | 8.2 | 2.8 | 3.9 | 56.4 | 59.6 |
| MEK | 70.2 | 7.6 | 4.4 | 2.5 | 62.4 | 67.5 |
| Methyl Acetate | 171.0 | 7.6 | 3.5 | 3.7 | 55.7 | 57.6 |
| Ethyl Acetate | 86.0 | 7.7 | 2.6 | 3.5 | 61.1 | 57.6 |
| Isobutyl Acetate | 12.5 | 7.4 | 1.8 | 3.1 | 63.8 | 70.9 |
| Methanol | 100.0 | 7.4 | 6.0 | 10.9 | 47.0 | 58.3 |
| Ethanol | 43.0 | 7.9 | 4.4 | 9.7 | 45.0 | 70.3 |
| IPA | 32.8 | 7.7 | 3.0 | 8.0 | 49.0 | 50.3 |
| 2-Butanol | 9.0 | 7.4 | 2.8 | 7.8 | 67.1 | 60.3 |
| Heptane | 40.0 | 7.4 | 0.0 | 0.0 | 78.5 | 86.8 |
| Toluene | 38.0 | 8.8 | 0.7 | 1.0 | 58.4 | 60.9 |
| Isopar C | 37.8 | 7.2 | 0.0 | 0.0 | 65.8 | 76.2 |
| Isopar E | 15.7 | 7.3 | 0.0 | 0.0 | 63.1 | 68.7 |

Percent evaporation of transfluthrin in the wind tunnel are shown in Table 12 for filter paper and Barex samples including the properties of the solvents such as Hansen's three dimensional solubility parameters (dispersive, polar, and hydrogen bonding components), and vapor pressures. It is evident that solvents affect the release rate of transfluthrin in a significant way. Evaporation of transfluthrin for Barex strips lies anywhere between 50% and 87% depending on the solvent used and for filter paper, it lies in the range 45% to 79%.

A detailed statistical analysis was carried out to identify significant linear relationships between the response variables and independent variables. In order to facilitate developing a multiple linear regression model, correlation coefficients between the four "predictor" variables, namely, "VP", "Hansen D", "Hansen P", and "Hansen H" (Vapor pressure, and dispersive, polar, and hydrogen bonding components of Hansen's 3D solubility parameters) were calculated and are shown in Table 13.

TABLE 13

Correlation coefficients between predictor variables

| | VP (mm) | Hansen D | Hansen P | Hansen H |
|---|---|---|---|---|
| VP (mm) | 1.0000 | | | |
| Hansen D | 0.1495 | 1.0000 | | |
| Hansen P | 0.5539 | 0.0150 | 1.0000 | |
| Hansen H | 0.0616 | −0.0023 | 0.7486 | 1.0000 |

Correlation coefficients between "Hansen P" and "VP" and also between "Hansen P" and "Hansen H" are relatively high suggesting the strength of the linear association between these two variables is high. Hence, this "predictor" variable is not included in the multiple linear regression analysis since this would lead to multicolinearity problems and make it very difficult to disentangle the influence of the individual explanatory variables. The information that this variable would convey would be conveyed by "Hansen H" and "VP".

Multiple linear regression analysis was then carried out between the response variable of interest, namely, "% evap." and independent variables, namely, "VP", "Hansen H", and "Hansen D" using Microsoft Excel version 5.0c. ANOVA results indicate that the P-value (significance F) is low for filter paper and Barex samples suggesting that the regression in both cases is significant. An R2 value of 0.6757 implies that 67.57% of the variation in "% evap" is explained by the fitted multiple regression of this response variable on "VP", "Hansen D", and "Hansen H" for filter paper samples. Similarly for Barex samples, the model explains 47.74% of the variability. The remaining unexplained variation may be due to the noise in the data or due to some other yet to be identified property that has not been considered here. The P-values for each of the independent variables suggest how strong the linear relationship is between the response variable and the predictor variable. P-values are considerably lower for "Hansen H" while they are relatively large for "VP" suggesting that the linear relationship is strongest between the response variable "% evap" and "Hansen H" while it is weakest with respect to "VP". The model equations obtained from the analysis are shown in Table 14.

TABLE 14

Multiple Linear Regression Models

For Filter Paper

% evap. = −0.03183 VP (mm) − 6.22466 Hansen D − 1.72725 Hansen H + 116.34228

For Barex

% evap. = −0.05412 VP (mm) − 6.4257 Hansen D − 1.26108 Hansen H + 122.69958

The negative slopes in the regression models suggest that the release rates are highest when solvents with low vapor pressure, low Hansen hydrogen bonding parameters, and low Hansen dispersive parameter are selected. A direct comparison of these coefficients between filter paper and Barex samples suggest that the release rates from filter papers are more strongly dependent on hydrogen bonding component of the solubility parameter than those from Barex while the effect of vapor pressure is reverse. The effect of Hansen dispersive component is very similar on both substrates.

The regression model developed above is used to predict "% evap." values at various solvent properties. Based on this model and the values of "% evap", most preferable, second most preferable, third most preferable, and least preferable ranges of solvent properties are identified (see Table 15). This identification is based on how close the range of "% evap" values are for both filter paper and Barex to that which corresponds to an ideal solvent which has negligible volatility, a dispersive component of 7.2 and no hydrogen bonding component. Again, one should note that these "% evap" values are used only to compare one with another and the actual evaporation rates may be higher or lower depending on the ambient conditions.

TABLE 15

Regression model predictions

| Preferable Range | Vapor Pressure in mm Hg | Hansen's Solubility Parameters: Dispersive Component | Hansen's Solubility Parameters: Hydrogen Bonding | % Evaporation from Regression Model: Filter paper | % Evaporation from Regression Model: Barex |
|---|---|---|---|---|---|
| Ideal | −0 | 7.2 | −0 | 71.5 | 76.4 |
| Most preferable | ≦20 | ≦7.4 | ≦2 | ≧66.2 | ≧71.5 |
| Second most preferable | ≦50 | ≦7.6 | ≦4.0 | ≧60.5 | ≧66.1 |
| Third most preferable | ≦100 | ≦8.0 | ≦6.0 | ≧53.0 | ≧58.3 |
| Least preferable | ≦200 | ≦8.8 | ≦12 | ≧34.5 | ≧40.2 |

Based on the investigation carried out, it was discovered that:

Solvents affect the release rate of transfluthrin in a significant way even though most of the solvent evaporates during the initial drying phase, the parameters that determine the effectiveness of the solvent are Hansen's hydrogen bonding parameter, Hansen's dispersive component, and volatility. Solvents with low values for these parameters are most effective in releasing transfluthrin from filter paper and Barex substrates, and the release rate is more strongly dependent on hydrogen bonding component for the filter paper than that for Barex.

The usefulness of these findings lie in recognizing its applications in preparing effective dilute intermediate solutions that can be sold as "repellent solutions" for consumer applications. The consumer can spray the solution which is made with a solvent that releases transfluthrin most effectively when sprayed on any surface such as cemented wall, a window pane, or a polished wooden surface.

EXAMPLE 6

Large Chamber Tests and Field Studies (a) Lab Studies in Large Chamber

The chamber test protocol was developed to realistically model actual use conditions for the insect control article of the invention. A closed, generally featureless, approximately 28 $m^3$, box-like test chamber is used, the size of a small room. Six mosquito knockdown cages are distributed vertically within the test chamber, suspended from poles adjacent to opposite test chamber side walls, where they can be observed from outside the test chamber through chamber windows. Mosquitos in the cages are observed during a test to evaluate the ability of a material being tested to knock down mosquitoes. An insect "knocked down" is one that is incapable of flying and usually is moribund in appearance. The insect may or may not actually be dead. The knockdown cages are cylindrical, approximately 6 cm long and 8 cm in diameter, and have screened but otherwise open ends.

Two repellency mosquito cages are also provided. The repellency cages are box-like screened cages, approximately 73 cm long and 16 cm square in cross section. All of the walls of the repellency cages are screened but otherwise generally open. Each repellency cage is divided by a clear plastic partition into a first holding area, which occupies approximately 45 cm of the length of the cage, and a second holding area, which occupies the remaining 28 cm. The plastic portion has a 4 cm diameter hole in its center that provides the only route by which mosquitoes may pass between the two holding areas. The repellency cages are mounted in a test chamber wall, with the plastic partition located in the plane of the test chamber wall, and are so oriented that the first holding area projects inwardly, into the test chamber, while the second holding area projects through the test chamber wall, out into normal room air.

A mouse cage essentially identical to a mosquito knockdown cage is mounted on the end of the first holding chamber of each repellency test cage that faces toward the interior of the test chamber. The mouse cage is separated from the repellency cage only by a mosquito-proof screen. One mouse is placed in the mouse cage during a test to provide an attractant for mosquitoes being held in the repellency test cage. Mosquitoes in the first holding area of a repellency cage thus are attracted toward the mouse, on the one hand, and repelled by the insect control article being tested, on the other hand.

When a test is run, fifty female mosquitoes are placed in the first holding area of each mosquito cage, with the partition hole closed by a removable door. Ten female mosquitoes are placed in each knock-down cage. The insect control article to be tested is placed centrally within the test chamber and the air flow is initiated. At timed intervals up to a total testing period of two hours, each knock-down cage and each repellency cage is visually examined, and the location, number, and condition of the mosquitoes are noted. The number of mosquitoes that have been driven to the second holding area provides a measure of the repellency of the insect control article being tested. The number of mosquitoes knocked-down in the knock-down cages is also recorded. The general success of an insect control article is judged by both the mosquitoes repelled and those knocked down, in that both effects reduce the total number of mosquitoes available for biting.

Barex strips 103 sq. cm. inches in size were coated with 5 mg of transfluthrin and tested for knock-down and repellency efficacy against caged, adult, female Aedes aegypti mosquitoes. The strips tested were both fresh and eight hour pre-used samples in a 0–2 hour test. Each strip was secured to a fan that was running at 3.5 m/s. A commercial mosquito coil was also tested without a running fan in the same chamber. Knock-down results are shown in Table 16 and repellency efficacy is shown in Table 17.

TABLE 16

| Mean percent knockdown (0–2 hr) | | | | | |
|---|---|---|---|---|---|
| Sample | 15 min | 30 min | 60 min | 120 min | 24 hr mortality |
| Barex Fresh | 0 | 33 | 95 | 100 | 96 |
| Barex-8 hr | 1 | 9 | 78 | 98 | 96 |
| Mosquito coil | 47 | 63 | 91 | 100 | 98 |
| Control | 0 | 0 | 0 | 0 | 0 |

TABLE 17

| Mean percent unavailable for biting (0–2 hr) | | | | |
|---|---|---|---|---|
| Sample | 15 min | 30 min | 60 min | 120 min |
| Barex Fresh | 38 | 70 | 88 | 95 |
| Barex-8 hr | 26 | 61 | 80 | 91 |
| Mosquito coil | 58 | 89 | 100 | 100 |
| Control | 0 | 1 | 2 | 4 |

The repellent strips, both fresh and aged, provide comparable knockdown and biting inhibition efficacy to that of a standard or conventional mosquito coil containing 0.3% d-cis, trans allethrin. The 8 hour aged strips were also sent to analytical for residual analysis. Results, as summarized in Table 18, indicate that the average release of transfluthrin during the 8 hour period is ~0.2 mg/hr. A release rate of ~0.2mg/hr transfluthrin from repellent strips thus provides biological efficacy comparable to that of a conventional commercially sold mosquito coil.

TABLE 18

| Analytical results | |
|---|---|
| Barex-Fresh | Residual level 5.2 mg |
| Barex-8 hr | Residual level 3.7 mg |
| Transfluthrin loss in 8 hr | 1.5 mg |
| Release rate of Transfluthrin | ~0.2 mg/hr |

Lab studies were also conducted on a portable electric device where a corrugated disc was impregnated with 280 mg of transfluthrin. The disc was placed in a device which has a fan that runs on a battery. Air flows through the holes of the disc releasing the transfluthrin into the environment. Lab studies were conducted on this unit to determine its efficacy. Results, as shown in Tables 19 and 20, indicate that the portable electric unit performs as good as a commercially sold mosquito repellent mat at both 1.6 volts and 1.3 volts. Weight loss experiments were also conducted to determine the release rates from this unit. When the unit was run at 80° F. for 180 hours at a voltage of 1.43 volts, a residual level of 233 mg of transfluthrin was detected on a refill unit that was initially loaded with 280 mg. These two studies together suggest that a release rate of 0.26 mg/hr provides mosquito repellency and knockdown efficacy as good as a standard repellent mat in the lab test chamber.

TABLE 19

| Mean percent unavailable for biting (0–2 hrs) at 80° F. | | | | |
|---|---|---|---|---|
| Volts | 15 min | 30 min | 60 min | 120 min |
| 1.6 | 4 | 11 | 47 | 82 |
| 1.3 | 6 | 7 | 45 | 82 |
| Standard Mat (36 mg Py. Forte* on Vape Fumakilla heater) | 5 | 39 | 81 | 86 |

TABLE 20

Mean percent knockdown (0–2 hrs) at 80° F.

| Volts | 15 min | 30 min | 60 min | 120 min | % Dead |
|---|---|---|---|---|---|
| 1.6 | 3 | 38 | 61 | 91 | 80 |
| 1.3 | 3 | 16 | 49 | 86 | 86 |
| Standard Mat (36 mg Py. Forte* on Vape Fumakilla heater) | 7 | 47 | 73 | 81 | 58 |

*Pynamin Forte is "3-allyl-2-methyl cyclopenta-2-en-4-on-1-yl D-cis/trans-Chrysanthemate".

The large chamber studies thus indicate that a release rate of 0.2–0.26 mg/hr of transfluthrin can provide knockdown and repellency performance to achieve practical control and perform as well as a conventional mosquito coil or a standard mosquito repellent electric mat.

(b) Field Studies

Field trials against Culex quinquefasciatus were conducted in living rooms of residential houses in a squatter area at Ujung Batu, Butterworth on the Northwest peninsula of Malaysia on plastic strips coated with transfluthrin. Indoor mosquitoes collection in this area during the pre-treatment trials indicated that more than 90% of the mosquitoes collected were Culex quinquefasciatus. A total of four configurations were tested.

Config. A 2 sheets hung together on each of four walls

Config. B 1 sheet hung on each four walls

Config. C 1 sheet hung on each two opposite walls

Config. D 1 sheet hung on a wall

Each of the sheets above were 0.7 sq. ft. in size, made of 2 mil Barex film, and was coated with 35 mg transfluthrin (55 $\mu g/cm^2$ coating density). The average volume of the rooms where the test is conducted is 75.5 cubic meters (equivalent to approximately 16 ft.×10 ft.). The human baits were seated 1–2 meters away from all the treated sheets and the efficacy was evaluated using the human bare-leg catch technique during the first 0–2 hours, 24 hours, 96 hours, and 168 hours the placing of the test sheets in the rooms.

These tests were conducted under a rigorous test environment. The predominant species collected during the trials was Culex quinquefasciatus which are most tolerant to pyrethroid based household insecticide products among the common mosquitoes found in the living premises in tropical and subtropical regions globally. Due to the local weather changes, the squatter area chosen for the trials indicated lower indoor mosquito density during the pretreatment and treatment trials.

Results showed that Configuration A was most effective throughout the 7 days application with overall reduction of landing/biting of more than 78% under rigorous tropical environment. All the strips tested in the field were analyzed for residual levels to determine the average release rates so as to compare them with biological efficacy. Results are shown in Table 21.

TABLE 21

Malaysia field study results

| | Percent Reduction in Mosquito Biting | | | | Transfluthrin Release | |
|---|---|---|---|---|---|---|
| | 0–1 hr | 1–2 hr | 2–3 hr | Total | mg/hr | $\mu g/hr/cm^2$ |
| Method A (8 strips) | 78.9 | 80.5 | 93.2 | 84.0 | 1.46 | 0.28 |
| Method B (4 strips) | −9.0% | 8.9% | 73.5 | 34.2 | 0.79 | 0.31 |
| Method C (2 strips) | 19.4 | 35.1 | 68.6 | 42.6 | 0.40 | 0.31 |
| Method D (1 strip) | 28.2 | 28.2 | 43.8 | 37.8 | 0.18 | 0.28 |

The test conditions for the Malaysia field study were very demanding. The rooms where the tests were conducted were large and most of these were interconnected with other rooms in the house. These rooms also have ventilated windows facilitating free air exchanging with the outside environment and hence product losses. The doors were also open during the day time further increasing the product losses. Such open areas lead to wastage of the product especially during the day time when the mosquito biting is not a problem. Even under these demanding conditions, a transfluthrin release rate of 0.18 mg/hr was sufficient to achieve practical control.

EXAMPLE 7

Dose Response Studies

Barex and filter paper samples coated with different dose levels of transfluthrin were tested in the glass chamber for knockdown efficiency. Results are shown in the Tables 22 and 23. These results suggest that biological efficacy is almost constant for Barex in the range of 1 $\mu g/cm^2$ to 340 $\mu g/cm^2$. The efficacy is marginally lower at a dose level of 1 $\mu g/cm^2$ and considerably lower at a dose level of 0.1 $\mu g/cm^2$. On the other hand, the filter papers show a dependency on dose level when the value falls below 50 $\mu g/cm^2$ level. Above this, the response is similar up to as much as 2500 $\mu g/cm^2$.

TABLE 22

Dose response on Barex

| Transfluthrin Level on 16 sq. in Area | Coating Density ($\mu g/cm^2$) | Dead (%) | KD50 (min) | KD80 (min) |
|---|---|---|---|---|
| .01 mg Barex | 0.097 | 0 | >20 | >20 |
| .1 mg Barex | 0.969 | 0 | 8.25 | 11.33 |
| 1 mg Barex | 9.688 | 87 | 5.9 | 7.7 |
| 5 mg Barex | 48.438 | 100 | 4.6 | 6.8 |
| 10 mg Barex | 96.875 | 90 | 4.5 | 6.8 |
| 25 mg Barex | 242.188 | 100 | 5.5 | 8.2 |
| 35 mg Barex | 339.063 | 100 | 5.8 | 6.8 |

TABLE 23

Dose response on filter paper

| Transfluthrin Level on 16 sq. in Area | Coating Density ($\mu g/cm^2$) | Dead (%) | KD50 (min) | KD80 (min) |
|---|---|---|---|---|
| 1 mg filter paper | 9.688 | 13 | 20.0 | 20.0 |
| 5 mg filter paper | 48.438 | 57 | 8.0 | 11.4 |
| 25 mg filter paper | 242.188 | 77 | 6.7 | 7.8 |

TABLE 23-continued

Dose response on filter paper

| Transfluthrin Level on 16 sq. in Area | Coating Density ($\mu g/cm^2$) | Dead (%) | KD50 (min) | KD80 (min) |
|---|---|---|---|---|
| 100 mg filter paper | 968.752 | 73 | 6.5 | 8.3 |
| 250 mg filter paper | 2421.880 | 80 | 7.3 | 8.6 |

The typical release rate for obtaining effective protection from mosquito biting is about 0.2 mg/hr (see Tables 16, 17, and 18). The release rate from a Barex strip hung on a wall as a poster in a room with no forced convection currents is about 0.3 $\mu g/hr/cm^2$ (see Table 21). With this knowledge of the required strip area for generating the minimum required transfluthrin release rate, coating densities can then be adjusted to obtain a specific product life as shown in Table 24. These product lives are applicable as long as the strip is exposed under the conditions specified.

TABLE 24

Estimated product life at various coating densities for a passive Barex strip

| Coating Density ($\mu g/cm^2$) | Product Life |
|---|---|
| 1.0 | 3 hours 20 min. |
| 2.4 | 1 day (8 hours/day) |
| 16.8 | 7 days (8 hours/day) |
| 36.0 | 15 days (8 hours/day) |
| 72.0 | 30 days (8 hours/day) |
| 144.0 | 60 days (8 hours/day) |
| 216.0 | 90 days (8 hours/day) |

A strip area of 667 sq. cm. (0.72 sq. ft.) at any of the coating densities above will release transfluthrin at the rate of 0.2 mg/hour adequate to provide protection from mosquito biting comparable to a mosquito coil or a mosquito repellent electric mat. Convenient coating densities range from 2.4 $\mu g/cm^2$ to 72 $\mu g/cm^2$ as this range corresponds to product life ranging from 1 day to 1 month, although efficacy is achieved at all coating densities above 1 $\mu g/cm^2$ and particularly throughout a range of 1 $\mu g/cm^2$ to 250 $\mu g/cm^2$.

Industrial Application

Materials and methods for practical control of mosquitoes and other insect pests have been shown, together with means for manufacture and use.

I claim:

1. An insect control article to control flying insects, comprising a non-porous, non-absorbing substrate and a coating on said substrate of an active insect control ingredient available for passive evaporation, wherein the active insect control ingredient is selected from the group consisting of transfluthrin, tefluthrin, and combinations thereof, and wherein solubility of the active insect control ingredient in the non-absorbing substrate is less than or equal to about 40 $\mu g/cm^2$ of substrate surface area, and the coating is formed by applying a solution of said active insect control ingredient and a solvent on said substrate, said solvent having a vapor pressure of less than or equal to 100 mm Hg and a Hansen's hydrogen bonding parameter of less than or equal to 6.0, and thereafter removing said solvent to provide said active insect control ingredient at a dose level of from 2.4 $\mu g/cm^2$ to 72 $\mu g/cm^2$ of substrate surface area.

2. The insect control article of claim 1 wherein the substrate is composed of a barrier material selected from the group consisting of a polymeric film, aluminum and glass.

3. The insect control article of claim 1, wherein the substrate is a polymeric film selected from the group consisting of acrylonitrile methacrylate copolymer, polyester, polyvinylidene chloride, high density polyethylene, nylon, polypropylene, polyvinyl alcohol, and ethylene vinyl alcohol films.

4. The insect control article of claim 1, wherein the non-absorptive substrate has a surface selected from the group consisting of untextured, textured, mesh, grooved, and reticulated.

5. The insect control article of claim 1, wherein the insect control article includes hanger means for hanging the coated substrate in a suitable environment for use.

6. The insect control article of claim 1 wherein the non-absorptive substrate has a surface area not less than 0.7 $m^2$.

7. The insect control article of claim 1, wherein the active insect control ingredient comprises transfluthrin.

8. The insect control article of claim 1, wherein the active insect control ingredient comprises tefluthrin.

9. The insect control article of claim 1, wherein the active insect control ingredient has a release rate of at least about 0.2 mg/hr.

10. The insect control article of claim 1 wherein the solubility of the active insect control ingredient in the substrate is less than or equal to about 20 $\mu g/cm^2$ of substrate surface area.

* * * * *